(12) United States Patent
Heller et al.

(10) Patent No.: US 10,597,691 B2
(45) Date of Patent: Mar. 24, 2020

(54) ISOTHERMAL AMPLIFICATION UNDER LOW SALT CONDITION

(71) Applicant: General Electric Company, Schenectady, NY (US)

(72) Inventors: Ryan Charles Heller, Guilderland, NY (US); John Richard Nelson, Clifton park, NY (US); Paresh Lakhubhai Patel, Cardiff (GB); Alison Myfanwy Wakefield, Cardiff (GB); Stephen James Capper, Cardiff (GB)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/408,509

(22) Filed: Jan. 18, 2017

(65) Prior Publication Data

US 2017/0121747 A1    May 4, 2017

Related U.S. Application Data

(62) Division of application No. 14/225,887, filed on Mar. 26, 2014, now Pat. No. 9,587,263.

(51) Int. Cl.
    *C12P 19/34*    (2006.01)
    *C12Q 1/6844*   (2018.01)

(52) U.S. Cl.
    CPC ............ *C12P 19/34* (2013.01); *C12Q 1/6844* (2013.01)

(58) Field of Classification Search
    CPC ............ C12Q 1/6844; C12Q 2531/119; C12Q 2525/179; C12Q 2527/125; C12Q 2527/137
    See application file for complete search history.

(56) References Cited

U.S. PATENT DOCUMENTS

| | | | |
|---|---|---|---|
| 7,022,835 B1 | 4/2006 | Rauth et al. | |
| 7,785,790 B1 | 8/2010 | Church et al. | |
| 2002/0068363 A1 | 6/2002 | Stemmer | |
| 2004/0248105 A1 | 12/2004 | Kumar | |
| 2005/0186602 A1 | 8/2005 | Kim et al. | |
| 2005/0208510 A1 | 9/2005 | Latham et al. | |
| 2006/0154286 A1* | 7/2006 | Kong | C12P 19/34 435/6.12 |
| 2007/0269819 A1 | 11/2007 | Kim et al. | |
| 2009/0130720 A1 | 5/2009 | Nelson et al. | |
| 2011/0195457 A1 | 8/2011 | Nelson et al. | |
| 2011/0281776 A1 | 11/2011 | Eshoo et al. | |
| 2013/0210078 A1* | 8/2013 | Nelson | C12P 19/34 435/91.2 |

FOREIGN PATENT DOCUMENTS

WO    2004/058987 A2    7/2004

OTHER PUBLICATIONS

Quick Ligation Kit, New England Biolabs, downloaded from NEB website, Mar. 5, 2018, pp. 1-3.*
Perez-Brocal et al., "Study of the Viral and Microbial Communities Associated With Crohn's Disease: A Metagenomic Approach", Clinical and Translational Gastroenterology, vol. 6, Issue 4, Jun. 2013; 16 Pages.
Chinese Office Action for CN Application No. 201580015896.3 dated Apr. 3, 2019 (11 pages with English translation).
Ballantyne et al., "Molecular Crowding Increases the Amplification Success of Multiple Displacement Amplification and Short Tandem Repeat Genotyping," Analytical Biochemistry, 2006, 355:298-303.
Japanese Office Action for JP Application No. 2016-559274 dated May 10, 2019 (7 pages with English translation).
Indian Examination Report for IN Application No. 2016/17026985 dated Jan. 31, 2020 (7 pages).
Pan et al., "A Procedure for Highly Specific, Sensitive, and Unbiased Whole-Genome Amplification," PNAS, 2008, 105 (40):15499-15504.
Tong et al., "Multiple Strategies to Improve Sensitivity, Speed and Robustness of Isothermal Nucleic Acid Amplification for Rapid Pathogen Detection," BMC Biotechnology, 2011, 11:50 (7 pages).

* cited by examiner

*Primary Examiner* — David C Thomas
(74) *Attorney, Agent, or Firm* — Eversheds Sutherland (US) LLP

(57) ABSTRACT

Provided herein are methods and kits for isothermal nucleic acid amplifications that use a target nucleic acid template; a reaction mixture comprising a DNA polymerase having a strand displacement activity, a deoxyribonucleoside triphosphate (dNTP) mixture, a primer with a 3' end and a 5' end, a molecular crowding reagent, and a buffer solution for amplifying the target nucleic acid template. The buffer solution maintains a low salt concentration of the reaction mixture, and wherein the salt concentration results in a melting temperature ($T_m$) of the primer at least 10° C. below the reaction temperature. The amplification is effected under isothermal condition.

18 Claims, 3 Drawing Sheets

ISOTHERMAL AMPLIFICATION UNDER LOW SALT CONDITION

CROSS REFERENCE TO RELATED APPLICATIONS

This application is a division of U.S. patent application Ser. No. 14/225,887, filed on Mar. 26, 2014, entitled ISOTHERMAL AMPLIFICATION UNDER LOW SALT CONDITION, which is hereby incorporated by reference in its entirety.

FIELD OF INVENTION

The invention generally relates to methods and kits for performing isothermal amplification reactions employing molecular crowding reagents under low salt conditions.

BACKGROUND

DNA amplification is a process of replicating a target double-stranded DNA (dsDNA) to generate multiple copies. Since individual strands of a dsDNA are antiparallel and complementary, each strand may serve as a template strand for the production of its complementary strand. The template strand is preserved as a whole or as a truncated portion and the complementary strand is assembled from deoxyribonucleoside triphosphates (dNTPs) by a DNA polymerase. The complementary strand synthesis proceeds in the 5'→3' direction starting from the 3' terminal end of a primer sequence that is hybridized to the template strand. A variety of efficient nucleic acid amplification techniques are currently available such as polymerase chain reaction (PCR), ligase chain reaction (LCR), self-sustained sequence replication (3SR), nucleic acid sequence based amplification (NASBA), strand displacement amplification (SDA), multiple displacement amplification (MDA), or rolling circle amplification (RCA). Many of these techniques generate a large number of amplified products in a short span of time.

Whole-genome amplification (WGA) involves non-specific amplification of a target DNA. WGA is often achieved by MDA employing random oligonucleotide primers (e.g., NNNNN*N) for priming DNA synthesis at multiple locations of the target DNA along with a high-fidelity DNA polymerase having a strand displacing activity (e.g., Phi29 polymerase). Even though currently available commercial WGA systems such as GenomiPhi (GE Healthcare, USA) and RepliG (Qiagen) kits provide optimal results with an input DNA of 1 nanogram or more, performance of these systems is poor when the target DNA is available only in smaller quantities or when amplification of DNA from a few or single cells is performed.

Despite these advancements, there remains a need for developing more efficient whole-genome nucleic acid amplification methods that have lower bias in terms of sequence coverage and produce lower levels of non-specific, background amplification. Amplification of trace amounts of target DNA using conventional methods often results in incomplete amplification of DNA sequences leaving "drop-outs" in sequence coverage and amplification bias wherein DNA sequences are amplified unevenly. Further, products of the amplification reaction (amplicons) may often anneal among themselves leading to the generation of undesirable chimeric products. Efficient methods for non-specifically amplifying trace amounts of target DNA are therefore highly desirable.

BRIEF DESCRIPTION

In some embodiments, nucleic acid amplification methods are provided that utilize a molecular crowding reagent under low salt condition and a primer with low melting temperature for amplifying a target nucleic acid to generate amplicons.

In some embodiments, an isothermal amplification method for producing at least one amplicon based on a target DNA is provided. The method comprises the steps of providing a target nucleic acid template and contacting the target nucleic acid template with a reaction mixture comprising a DNA polymerase having a strand displacement activity, a deoxyribonucleoside triphosphate (dNTP) mixture, a primer with a 3' end and a 5' end, a molecular crowding reagent, and a buffer solution, wherein the buffer solution maintains a salt concentration of the reaction mixture between 10 to 30 mM. The amplification is effected under isothermal condition at a constant reaction temperature, wherein the salt concentration optimizes a melting temperature ($T_m$) of the primer at least 10° C. below the reaction temperature.

In some embodiments, an isothermal amplification method for producing at least one amplicon based on a target DNA is provided. The method comprises the steps of, providing a target nucleic acid template; contacting the target nucleic acid template with a reaction mixture comprising a DNA polymerase having a strand displacement activity, a deoxyribonucleoside triphosphate (dNTP) mixture, a primer with a 3' end and a 5' end, polyethylene glycol as a molecular crowding reagent, and a buffer solution, wherein the buffer solution maintains a salt concentration of the reaction mixture at 15 mM. The amplification is effected under isothermal condition at a constant reaction temperature of 30° C., wherein the salt concentration optimizes a melting temperature ($T_m$) of the primer at least 10° C. below the reaction temperature.

In some embodiments, kits for isothermal DNA amplification are provided. The kits comprise a DNA polymerase having strand displacement activity, a molecular crowding reagent; and a buffer that provides a final salt concentration between 10 mM to 20 mM during amplification.

DRAWINGS

These and other features, aspects and advantages of the invention will become better understood when the following detailed description is read with reference to the accompanying figures.

DETAILED DESCRIPTION

Figure 1A:
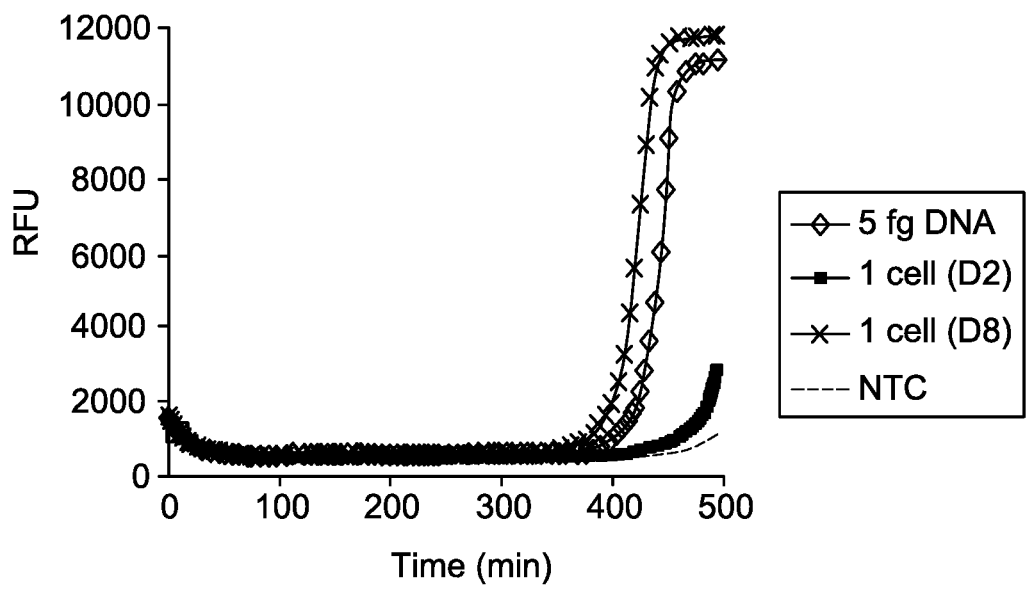
FIG. 1A illustrates the kinetics of an MDA reaction in absence of low salt and molecular crowding reagents.

To more clearly and concisely describe and point out the subject matter of the claimed invention, the following definitions are provided for specific terms that are used in the following description and appended claims.

As used herein, the term "target DNA" refers to a DNA sequence of either natural or synthetic origin that is desired to be amplified in a DNA amplification reaction. The target DNA acts as a template in a DNA amplification reaction. Either a portion of a target DNA or the entire region of a target DNA may be amplified by a DNA polymerase in a DNA amplification reaction to produce amplification products or amplicons. Amplicons may include multiple copies of the target DNA or multiple copies of sequences that are complementary to the target DNA. The target DNA may be obtained from a biological sample in vivo or in vitro. For example, the target DNA may be obtained from a bodily fluid (e.g., blood, blood plasma, serum, or urine), an organ, a tissue, a cell, a sectional portion of an organ or tissue, a cell isolated from a biological subject (e.g., a region containing diseased cells, or circulating tumor cells), a forensic sample or an ancient sample. The biological sample that contains, or is suspected to contain, the target DNA may be of eukaryotic origin, prokaryotic origin, viral origin or bacteriophage origin. For example, the target DNA may be obtained from an insect, a protozoa, a bird, a fish, a reptile, a mammal (e.g., rat, mouse, cow, dog, guinea pig, or rabbit), or a primate (e.g., chimpanzee or human). The target DNA may also be a complementary DNA (cDNA) that is generated from an RNA template (e.g., mRNA, ribosomal RNA) using a reverse transcriptase enzyme. A DNA product generated by another reaction, such as a ligation reaction, a PCR reaction, or a synthetic DNA may also serve as a suitable target DNA. The target DNA may be dispersed in solution or may be immobilized on a solid support, such as in blots, arrays, glass slides, microtiter plates, beads or ELISA plates.

As used herein the term "oligonucleotide" refers to an oligomer of nucleotides. A nucleotide may be represented by its letter designation using alphabetical letters corresponding to its nucleoside. For example, A denotes adenosine, C denotes cytidine, G denotes guanosine, U denotes uridine, and T denotes thymidine (5-methyl uridine). W denotes either A or T/U, and S denotes either G or C. N represents a random nucleoside and may be any of A, C, G, or T/U. A star (*) sign preceding a letter designation denotes that the nucleotide designated by the letter is a phosphorothioate-modified nucleotide. For example, *N represents a phosphorothioate-modified random nucleotide. A plus (+) sign preceding a letter designation denotes that the nucleotide designated by the letter is a locked nucleic acid (LNA) nucleotide. For example, +A represents an adenosine LNA nucleotide, and +N represents a locked random nucleotide. The oligonucleotide may be a DNA oligonucleotide, an RNA oligonucleotide or a DNA-RNA chimeric sequence. Whenever an oligonucleotide is represented by a sequence of letters, the nucleotides are in 5'→3' order from left to right. For example, an oligonucleotide represented by a letter sequence $(W)_x(N)_y(S)_z$, wherein x=2, y=3 and z=1, represents an oligonucleotide sequence WWNNNS, wherein W is the 5' terminal nucleotide and S is the 3' terminal nucleotide ("Terminal nucleotide" refers to a nucleotide that is located at a terminal position of an oligonucleotide sequence. The terminal nucleotide that is located at a 3' terminal position is referred as a 3' terminal nucleotide, and the terminal nucleotide that is located at a 5' terminal position is referred as a 5' terminal nucleotide).

As used herein the term "nucleotide analogue" refers to compounds that are structurally analogous to naturally occurring nucleotides. The nucleotide analogue may have an altered phosphate backbone, sugar moiety, nucleobase, or combinations thereof. Nucleotide analogues may be a synthetic nucleotide, a modified nucleotide, or a surrogate replacement moiety (e.g., inosine). Generally, nucleotide analogues with altered nucleobases confer, among other things, different base pairing and base stacking properties.

As used herein, the term "primer" or "primer sequence" refers to a linear oligonucleotide that hybridizes to a target DNA template to generate a target DNA:primer hybrid and to prime a DNA synthesis reaction. Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3 nucleotides long) do not form thermodynamically stable duplexes with target nucleic acid under such hybridization conditions. The upper limit is often determined by the possibility of having a duplex formation in a region other than the pre-determined nucleic acid sequence in the target nucleic acid. Generally, suitable primer lengths are in the range of about 3 nucleotides long to about 40 nucleotides long. The primer may be an RNA oligonucleotide, a DNA oligonucleotide, or a chimeric sequence.

As used herein, the term "random oligonucleotide" refers to a mixture of oligonucleotide sequences, generated by randomizing a nucleotide at any given location in an oligonucleotide sequence in such a way that the given location may consist of any of the possible nucleotides or their analogues (complete randomization). A random oligonucleotide when used as a random primer represents a random mixture of oligonucleotide sequences, consisting of every possible combination of nucleotides within the sequence. For example, a hexamer random primer may be represented by a sequence NNNNNN or $(N)_6$. A hexamer random DNA primer consists of every possible hexamer combinations of 4 DNA nucleotides, A, C, G and T, resulting in a random mixture comprising $4^6$ (4,096) unique hexamer DNA oligonucleotide sequences. Random primers may be effectively used to prime a nucleic acid synthesis reaction when the target nucleic acid's sequence is unknown or for whole-genome amplification reaction.

As described herein, "partially constrained oligonucleotide" refers to a mixture of oligonucleotide sequences, generated by completely randomizing some of the nucleotides of an oligonucleotide sequence (e.g., the nucleotide may be any of A, T/U, C, G, or their analogues) while restricting the complete randomization of some other nucleotides (e.g., the randomization of nucleotides at certain locations are to a lesser extent than the possible combinations A, T/U, C, G, or their analogues). A partially constrained oligonucleotide may be used as primer sequence. For example, a partially constrained DNA hexamer primer represented by WNNNNN, represents a mixture of primer sequences wherein the 5' terminal nucleotide of all the sequences in the mixture is either A or T. Here, the 5' terminal nucleotide is constrained to two possible combinations (A or T) in contrast to the maximum four possible combinations (A, T, G or C) of a completely random DNA primer (NNNNNN). Suitable primer lengths of a partially constrained primer may be in the range of about 3 nucleotides long to about 15 nucleotides long.

As used herein the dNTP mixture refers to a mixture deoxyribonucleoside triphosphates, where N is a random nucleotide including any of A, C, G, or T/U.

As used herein, the terms "strand displacing nucleic acid polymerase" or "a polymerase having strand displacement activity" refer to a nucleic acid polymerase that has a strand displacement activity apart from its nucleic acid synthesis activity. A strand displacing nucleic acid polymerase can continue nucleic acid synthesis on the basis of the sequence of a nucleic acid template strand by reading the template strand while displacing a complementary strand that is annealed to the template strand.

As used herein, multiple displacement amplification (MDA) refers to a nucleic acid amplification method, wherein the amplification involves the steps of annealing a primer to a denatured nucleic acid followed by DNA synthesis in which downstream double stranded DNA region(s) which would block continued synthesis is disrupted by a strand displacement nucleic acid synthesis through these regions. As nucleic acid is synthesized by strand displacement, single stranded DNA is generated by the strand displacement, and as a result, a gradually increasing number of priming events occur, forming a network of hyper-branched nucleic acid structures. MDA is highly useful for whole-genome amplification for generating high-molecular weight DNA from a small amount of genomic DNA sample with limited sequence bias. Any strand displacing nucleic acid polymerase that has a strand displacement activity apart from its nucleic acid synthesis activity (e.g., Phi29 DNA polymerase or a large fragment of the Bst DNA polymerase) may be used in MDA. MDA is often performed under isothermal reaction conditions, using random primers for achieving amplification with limited sequence bias.

As used herein, the term "rolling circle amplification (RCA)" refers to a nucleic acid amplification reaction that amplifies a circular nucleic acid template (e.g., single stranded DNA circles) via a rolling circle mechanism RCA is initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). RCA typically produces concatamers comprising tandem repeat units of the circular nucleic acid template sequence complement.

As used herein, the term "molecular crowding reagent" refers to the reagents or molecules, which alters the properties of other molecules in a solution. Examples of molecular crowding reagents include, but are not limited to, dextran or polyethylene glycol (PEG). Generally, the molecular crowding reagents have high molecular weight, or bulky structure which generates a crowded environment in a solution comprising other molecules. The molecular crowding reagents reduce the volume of solvent available for other molecules in the solution, which results in molecular crowding. In some embodiments, a high concentration of polyethylene glycol having a molecular weight of 6000 Da (PEG 6000) occupies a large proportion of the volume of a solution comprising other molecules. For example, PEG 6000 present in a reaction mixture comprising other reactants, wherein the PEG molecules occupy a large proportion of the solvent of the reaction mixture. The molecular crowding may alter the rates or equilibrium constants of the reactions. In some embodiments, wherein the melting temperature of the primer-template DNA duplex ($T_m$) decreases in presence of low salt concentration, that melting temperature is increased on addition of the molecular crowding reagents to the amplification reaction mixture.

As used herein, the term "reaction temperature" refers to a temperature that maintains during the amplification reaction. The embodiments of the present invention comprise an isothermal amplification reaction, wherein the temperature of the reaction is constant. The entire isothermal amplification reaction is effected under the reaction temperature, such as the reaction temperature for the isothermal amplification reaction using GenomiPhi is about 30° C. The reaction temperature varies with varying conditions, including but not limited to, use of different polymerases, size of the primer or template, use of additional salts or stabilizing agents.

As used herein, the term "melting temperature" ($T_m$) refers to a temperature at which one-half of a primer-template nucleic acid duplex dissociates generating single stranded oligomers, or nucleic acids such as DNA. The stability of a primer-template DNA duplex may be measured by its $T_m$. Primer length and sequence are of significant in designing the parameters of a successful amplification. The melting temperature of nucleic acid duplex increases with its length and with increasing GC content. The concentration of $Mg^{2+}$, $K^+$ and solvents influence the $T_m$ of a primer. In one example, $T_m$ is in a range of 15.8 to 27.8° C. in presence of 85 mM $K^+/Na^+$ and GenomiPhi V2™, wherein the primer sequence is NNNNN*N. In another example, $T_m$ is in a range of 5 to 17° C. for single cell GenomiPhi™ in presence of 19 mM $K^+/Na^+$, wherein the primer sequence is NNNNN*N.

The methods and kits described herein are intended to efficiently amplify target nucleic acids with the additional advantage of reducing non-specific amplification of non-target nucleic acids (e.g., primer-dimers, chimeric nucleic acid products, etc.) that are observed with other methods of nucleic acid amplification. Without intending to be limited to a particular mechanism of action, the disclosed methods accomplish these goals by employing a molecular crowding reagent, a low salt condition and amplifying the nucleic acids under isothermal conditions.

One or more embodiments of a method comprise providing a target nucleic acid template, contacting the target nucleic acid template with a reaction mixture; and amplifying the target nucleic acid template under isothermal amplification condition at a constant reaction temperature. In these embodiments, the reaction mixture comprises a DNA polymerase having a strand displacement activity, a deoxyribonucleoside triphosphate (dNTP) mixture, a primer with a 3' end and a 5' end, a molecular crowding reagent, and a buffer solution, wherein the buffer solution maintains a salt concentration of the reaction mixture between 10 to 30 mM and wherein the salt concentration of the reaction mixture results in melting temperature ($T_m$) of the primer to at least 10° C. below the reaction temperature. As noted, the reaction temperature refers to a single temperature that is maintained constant during the isothermal amplification reaction.

As noted, the salt concentration of the reaction mixture affects melting temperature ($T_m$) of the primer-target nucleic acid duplex, wherein the resulting melting temperature is less than the reaction temperature. In one or more embodiments, the melting temperature of the primer-target nucleic acid duplex is decreased in presence of low salt condition in an amplification reaction. In one or more embodiments, the duplex melting temperature ($T_m$) of the oligonucleotide primer(s) is (are) 8-10° C. lower under low salt condition, as the stability of the Watson-Crick base pairing in the nucleic acid-primer hybrid may decrease under that condition. In one or more examples, the reaction rate increases in presence of PEG in the amplification reaction mixture under low salt concentration compared to the reaction rate of the same reaction in absence of PEG. The experimental observation established the fact that the amplification reaction had very slow reaction kinetics with decreasing salt concentration, such as between 10 to 15 mM. The reaction rate of the amplification reaction improves on addition of molecular crowding reagents, such as PEG, under the same low salt conditions. The melting temperature of the primers (oligomers) decreases at low salt concentration, which also decreases the reaction kinetics, wherein the kinetics of the amplification reaction further increases by adding molecular crowding reagents. The higher reaction temperature than the $T_m$ of a duplex may cause destabilization of the primer-template duplex and may melt the duplex, as the melting temperature of the primers are low under this low salt condition. However, unexpectedly, on addition of molecular crowding reagents, such as PEG, there is observed an increase in the reaction rate and the amplification reaction proceeds as other conventional amplification reaction, and therefore the primer-template duplex stabilizes at relatively higher temperature. For example, even when the melting temperature of the primer-template duplex is 15° C., the duplex is stabilized at 30° C. in presence of molecular crowding reagents under the low salt condition. The melting temperature of the same primer-template duplex decreases under low salt condition, and it may be decreased by 8-10° C. In some embodiments, the decreased $T_m$ of the duplex requires the amplification reaction to be performed at a lower temperature than that used in traditional amplification reactions.

As noted, the method comprises contacting the target nucleic acid template with a reaction mixture comprising a molecular crowding reagent. The molecular crowding reagent serves to increase the speed and efficiency of amplification reaction under stringent condition. The molecular crowding reagents may increase the rate of the reaction. In some embodiments, the low salt concentration optimizes the $T_m$ such that the $T_m$ is at least 10° C. lower than the reaction temperature, and the presence of molecular crowding reagents results desired non-biased amplification products with increased reaction rate.

The melting temperature of a primer-template duplex may be calculated using various standard methods. The melting temperature of the present method is calculated using the method described below. The calculations are only estimates the melting temperature and different factors may affect the melting temperature, including detergents, salt concentrations, counter ions or solvents. As the $T_m$ is modified by using a low salt condition, in some embodiments, the $T_m$ may refer to herein as a salt adjusted melting temperature ($T_m$). For the determination of $T_m$, a variation on two standard approximation calculations is used. For sequences less than 14 nucleotides the same formula as the basic calculation is use, with a salt concentration adjustment:

$$T_m=(wA+xT)*2+(yG+zC)*4-16.6*\log_{10}(0.050)+16.6*\log_{10}([Na^+])$$

wherein, w, x, y, and z are the number of bases A, T, G, C in the oligonucleotides sequence, respectively. The term $16.6*\log_{10}([Na^+])$ adjusts the $T_m$ for changes in the salt concentration, and the term $\log_{10}(0.050)$ adjusts for the salt adjustment at 50 mM Na$^+$. The reaction mixture may contain one or more monovalent and divalent salts which may have an effect on the $T_m$ of the oligonucleotides. As the sodium ions are much more effective at forming salt bridges between DNA strands and therefore have significant effect in stabilizing double-stranded DNA. The melting temperature (Tm) calculation assumes that the annealing occurs under the standard condition of 50 mM primer at pH7.0 in presence of monovalent cation (either Na+ or K+) with concentrations between 0.01 and 1.0 M, the non-symmetric sequences are at least 8 bases long and contain at least one G or C. (See Nakano et al, (1999) *Proc. Nucleic Acids Res.* 27:2957-65, and Warren A Kibbe, (2007) *Nucleic Acids Res.* 35: W43-W46 (webserver issue)).

The kinetics of amplification using MDA is increased by incorporation of molecular crowding reagents in the reaction mixture. The molecular crowding is a factor that determines the structure, stability and function of nucleic acids. In some embodiments, the structure and stability of the DNA duplexes are influenced by the molecular crowding reagents. The molecular crowding reagents may affect the nucleic acid structures, which may depend on the patterns of base-pairing or hydrogen bonding in the nucleic acid structure. Different size of the molecular crowding reagents has different effect on stabilization of the DNA duplexes, wherein the length of the DNA duplex also contributes to the stability. For example, polyethylene glycol (PEG) is a molecular crowding reagent which has varying molecular weight, and has different effect on the stability of the DNA duplex. In some embodiments, the amplification reaction rate increases on addition of PEG in presence of low salt condition.

In one or more embodiments, the molecular crowding reagent used in the amplification reaction is selected from a group consisting of a polyethylene glycol, Ficoll™, trehalose and combinations thereof. In one embodiment, the molecular crowding reagent comprises polyethylene glycol. The molecular crowding reagent may be selected from a group consisting of a PEG 2000, PEG 6000, PEG 8000 and combinations thereof. In some embodiments, the amplification reaction employs 2.5% PEG-8000 that increases the amplification rate compared to the standard amplification conditions, such as GenomiPhi™ condition.

In one or more embodiments of the nucleic acid amplification reactions, a high stringency hybridization condition may be employed to reduce undesired amplification products and artifacts. High stringency hybridization conditions refer to reaction conditions that impart a higher stringency to an oligonucleotide hybridization event than the stringency provided by conditions that are generally used for nucleic acid amplification reactions. Typically, nucleic acid amplification reaction is performed wherein the $T_m$ of the oligonucleotide primer(s) is/are within 10 degrees of the reaction temperature used for amplification. This allows the oligonucleotide primer(s) to bind stably to the template. Under high stringency conditions, the $T_m$ of the oligonucleotide primer(s) used is greater than the temperature that is 10 degrees lower than the reaction temperature. This may prevent stable binding of the primer to the template, and is not typically used for amplification reactions. For example, a high stringency hybridization condition may be achieved in a nucleic acid amplification reaction by increasing the reaction temperature or by decreasing the salt concentration. A combination of low salt (~15 mM) and the use of a molecular crowding reagent (e.g., 2.5% PEG-8000) provided increased reaction kinetics and more uniform coverage of amplified sequences, as shown in FIGS. 1A, 1B, 1C, 2 and 3.

As noted, the method comprises a step of contacting the target nucleic acid template with a reaction mixture comprising a buffer solution. The buffer solution used for amplification reaction may have 1 to 75 mM salt concentration. In some embodiments, the salt concentration is between 1 to 35 mM. In some embodiments, the buffer solution maintains a salt concentration of the reaction mixture between 10 to 30 mM. In one embodiment, the salt concentration of the reaction mixture is maintained at about 20 mM. In some other embodiments, the amplification reaction occurs under a lower concentration of salt compared to the conventional amplification methods. For example, 15 mM KCl is used for amplification as opposed to the 75 mM KCl used in traditional amplification reactions. Nucleic acid amplification reactions that utilize random hexamers are often carried out at about 75 mM salt concentration and at 30° C., wherein the embodiments of the method comprise the step of nucleic acid amplification reaction at about 15 mM salt concentration and 30° C., which is a high stringency hybridization condition. The amplification reaction under low salt concentration in the presence of molecular crowding agents improves the speed and sensitivity of the reaction when amplifying from trace nucleic acid samples.

In some embodiments, the duplex melting temperature ($T_m$) is decreased by about 5-10° C. under low salt concentration, but molecular crowding agents are added which allows the amplification reaction to be performed under more stringent conditions, such as at a higher temperature. Salt concentration may be varied depending on length of the primer as well as constituents of the nucleotides of the primer to result decreased melting temperature. The salt used for the present method may be monovalent salt, such as sodium or potassium.

In embodiments of the present method, the resulting melting temperature of the primer-template duplex at 75 mM salt concentration is in a range of 15-27° C., wherein the reaction is performed at 30° C. in presence of random hexamer primer and in the absence of molecular crowding agents. When the reaction condition is modified to 15 mM salt concentration at 30° C. reaction temperature, in presence of random hexamer primer and in the absence of molecular crowding agents, the resulting melting temperature of the primer-template duplex is in a range of 3-15° C., which is more than 15° C. lower than the reaction temperature. Under this 15 mM salt concentration condition, the reaction kinetics are expected to slow considerably. However, unexpectedly, the reaction rate increases in presence of PEG under 15 mM salt concentration, 30° C. reaction temperature, in presence of random hexamer primer compared to the reaction rate in absence of PEG under the same condition, which may be caused by better primer-template hybridization occurs in presence of PEG. In addition to better reaction kinetics, molecular crowding reagents (PEG) also result in producing better representative amplification product.

As noted, in some embodiments, an isothermal amplification method comprises the steps of providing a target DNA. Sufficient quantity of a target nucleic acid is one of the primary requirements for an amplification reaction to generate evenly amplified nucleic acid with correct sequence. Under standard GenomiPhi™ reaction conditions, the target nucleic acid of quantity greater than ~1-10 ng generates non-biased amplification products, whereas more biased amplification occurs throughout the genome when the input target nucleic acid quantity is less. Using less quantity of target nucleic acids, certain areas of the genome are amplified with reduced efficiency, wherein some of the areas of the genome are amplified with increased efficiency, resulting in non-uniform amplification product. The dropouts and high levels of amplification bias or missing sequences in the amplified products are reduced in spite of using a low quantity of input target nucleic acids, such as femtogram levels of input target nucleic acids in the present embodiments of the methods. One or more embodiments of the method reduces the probability of forming defective amplicons especially when attempting to amplify DNA from a single cell which contains a limited quantity of nucleic acid to start an amplification reaction. For example, human cells contain ~6.6 pg of DNA, wherein bacterial cells contain ~5 fg of DNA. Even after using a target nucleic acid of about 5 fg, which may be available from a single microbial cell, the present method of amplifying nucleic acids results in amplicons with low levels of incorrect sequences or amplification bias. In one or more embodiments, at least about 5 fg target nucleic acid template is provided, or essentially one microbial genome. In some examples, the amplification from a single bacterial cell, wherein at least about 5 fg of bacterial target nucleic acid is available, results in higher levels of target sequence and more representative amplification product under the condition of low salt and presence of molecular crowding reagent compared to the standard amplification method. In some other embodiments, the amplification from a single human cell, wherein at least about 6.6 pg of the human target nucleic acid is available, which results in more complete and representative amplification product under the same condition of low salt and molecular crowding reagent. In these embodiments, the amplification rates are also increased compared to the standard amplification conditions.

The target DNA may be linear template, nicked template or a circular template. It may be a natural or synthetic DNA. The target DNA may be a cDNA or a genomic DNA. The DNA template may be a synthetic template (e.g., a linear or nicked DNA circularized by enzymatic/chemical reactions), or it may be a plasmid DNA.

As noted, the primer used for the amplification method has a low melting temperature. For priming DNA synthesis, the amplification reaction often utilizes random hexamers with the sequence 5'-NNNN*N*N, where "N" represents a deoxyadenosine (dA), deoxycytidine (dC), deoxyguanosine (dG), or deoxythymidine (dT) and "*" represents a phosphorothioate linkage.

In one or more embodiments, the primer may be a specific primer sequence, a random primer sequence or a partially constrained random primer sequence. Specific primer sequences are complementary to a particular sequence that is present in the target DNA template, in the Watson-Crick base-pair. Specific oligonucleotide sequences may be employed in the primer, for example, for specifically amplifying a mitochondiral DNA in a mixture, a certain plasmid in a mixture, or certain genome region.

In some embodiments, the oligonucleotide sequence in the primer is a random primer sequence. In some embodiments, the length of the primers is between 5 to 9 nucleotides long. In one embodiment, the primer length is 6 nucleotides (hexamer). For example, the primer may be a random hexamer sequence. In embodiments of amplification reaction using random hexamer primer under the condition of 15 mM salt, 30° C. reaction temperature, the melting temperature of the primer-template duplex decreases to at least 10° C. below the reaction temperature.

Further, the random sequence may comprise one or more modified nucleotides and may comprise one or more phosphorothioate linkages. For example, the primer may be NN(N)mNN, where the integer value of m ranges from 0 to 36. In some embodiments, the integer value of m may range from 0 to 20. In some other embodiments, the integer value of m may range from 0 to 10. In some example embodiments, the oligonucleotide sequence may be a random tetramer, a random pentamer, a random hexamer, a random heptamer or a random octamer. The primer may comprise natural, synthetic or modified nucleotides, or nucleotide analogues. For priming DNA synthesis, the amplification reaction frequently utilizes random hexamers with the sequence 5'-NNNNN*N, where "N" represents a deoxyadenosine (dA), deoxycytidine (dC), deoxyguanosine (dG), or deoxythymidine (dT) and "*" represents a phosphorothioate linkage. In some embodiments, the primers are modified to minimize competing non-target nucleic acid (i.e., template DNA) amplification to modify the oligonucleotide primers in such a way as to inhibit their ability to anneal with one another.

Constrained-randomized hexamer primers that cannot cross-hybridize via intra- or inter-molecular hybridization (e.g., R6, where R=A/G) have been used for suppressing primer-dimer structure formation during nucleic acid amplification. These constrained-randomized primers, however, impart considerable bias in nucleic acid amplification reaction. Such primers are also of limited use for sequence-non-specific or sequence-non-biased nucleic acid amplification reactions (e.g., whole genome or unknown nucleic acid sequence amplification).

In some embodiments, the primer may comprise synthetic backbones or nucleotide analogues that confer stability and/or other advantages (e.g., secondary structure formation) to the primers (e.g., peptide nucleic acid or PNA), locked nucleic acid (LNA) or may comprise modified sugar moieties (e.g., xylose nucleic acid or analogues thereof).

In some embodiments, the primer comprises one or more LNA nucleotides. The speed and sensitivity of the amplification reaction, such as MDA may be improved when amplifying from trace nucleic acid samples using LNAs into the oligonucleotide primers. LNAs are a class of conformationally restricted nucleotide analogues that serve to increase the speed, efficiency, and stability of base pairing, thereby promoting the hybridization of the modified oligonucleotides to their target sequences in the nucleic acid of interest. LNA nucleotide contains a bicyclic furanose sugar unit locked in a ribonucleic acid-mimicking sugar conformation. The structural change from a deoxyribonucleotide (or a ribonucleotide) to the LNA nucleotide may be limited from a chemical perspective, for example, the introduction of an additional linkage between carbon atoms at 2' position and 4' position (e.g., 2'-C, 4'-C-oxymethylene linkage). The 2' and 4' position of the furanose unit in the LNA nucleotide may be linked by an O-methylene (e.g., oxy-LNA: 2'-O, 4'-C-methylene-β-D-ribofuranosyl nucleotide), a S-methylene (thio-LNA), or a NH-methylene moiety (amino-LNA), and the like. Such linkages restrict the conformational freedom of the furanose ring. In some embodiments, the primers comprising one or more LNA oligonucleotides display enhanced hybridization affinity towards complementary single-stranded RNA, single-stranded DNA or double-stranded DNA. Further, inclusion of LNA in the oligonucleotide may induce A-type (RNA-like) duplex conformations.

In some embodiments, the nucleic acid amplification uses random hexamer primers of the general structure 5'-+W+WNNN*S-3', where "+" precedes a locked nucleic acid base (i.e., "an LNA base"; for example, +A=an adenosine LNA molecule), "W" represents a mixture of only dA and dT, and "S" represents a mixture of only dC and dG. The "*" represents a phosphorothioate linkage between the two nucleotides. Since "W" bases are unable to stably pair with "S" bases, the formation of the oligonucleotide duplex is inhibited, which leads to decreased amplification of non-template nucleic acids.

In some embodiments, the primer employed for DNA amplification reaction may be resistant to nucleases, for example an exonuclease. For example, the primer may comprise one or more modified phosphate linkage (e.g., a phosphorothioate linkage) to render it exonuclease-resistant. In some embodiments, the primer comprises an exonuclease-resistant random oligonucleotide sequence. For example, the primer may have a random sequence such as NNNNN*N or NNNN*N*N.

In some embodiments, the primer is a partially constrained primer sequence. Non-limiting examples of partially constrained primer sequences, that have restricted randomization only at the terminal nucleotides include, but is not limited to, $W(N)_yS$, $S(N)_yW$, $D(N)_yG$, $G(N)_yD$, $C(N)_yA$, or $A(N)_yC$. The integer value of y may be in the range 2 to 13. In some embodiments, the value of y may be 2, 3, 4, or 5. In some example embodiments, a partially constrained primer sequence, $(W)_x(N)_y(S)_z$, wherein x, y and z are integer values independent of each other, and wherein value of x is 2 or 3, value of y is 2, 3, 4, or 5 and value of z is 1 or 2. The partially constrained primer sequence may comprise one or more nucleotide analogues. In some embodiments, the partially constrained primer sequence may have a terminally mismatched primer-dimer structure. For example, since W cannot base pair with S, there will be a terminal mismatch at both the 3' terminal nucleotides if the primer-dimer structure without any recessed ends is formed by inter-molecular hybridization. In some embodiments, the primer sequence is a nuclease-resistant, partially constrained sequence comprising a modified nucleotide, and having terminal mismatch primer-dimer structure.

In some embodiments, methods for producing at least one amplicon based on a target DNA comprise the steps of providing the target DNA, annealing at least a primer to the target DNA to generate a target DNA:primer hybrid, and extending the primer via an isothermal nucleic acid amplification reaction to produce at least one amplicon that is complementary to at least one portion of the target DNA.

The nucleic acid polymerase used for the isothermal amplification methods may be a proofreading or a non-proofreading nucleic acid polymerase. The nucleic acid polymerase may be a thermophilic or a mesophilic nucleic acid polymerase. Examples of DNA polymerases that are suitable for use in the methods include, but are not limited to, Phi29 DNA polymerase, hi-fidelity fusion DNA polymerase (e.g., *Pyrococcus*-like enzyme with a processivity-enhancing domain, New England Biolabs, MA), Pfu DNA polymerase from *Pyrococcus furiosus* (Strategene, Lajolla, Calif.), Bst DNA polymerase from *Bacillus stearothermophilus* (New England Biolabs, MA), Sequenase™ variant of T7 DNA polymerase, exo(−) $Vent_R$™ DNA polymerase (New England Biolabs, MA), Klenow fragment from DNA polymerase I of *E. coli*, T7 DNA polymerase, T4 DNA polymerase, DNA polymerase from *Pyrococcus* species GB-D (New England Biolabs, MA), or DNA polymerase from *Thermococcus litoralis* (New England Biolabs, MA).

In some embodiments, the nucleic acid polymerase used for the isothermal amplification is a strand displacing nucleic acid polymerase. The methods may employ a highly processive, strand-displacing polymerase to amplify the target DNA under conditions for high fidelity base incorporation. A high fidelity DNA polymerase refers to a DNA polymerase that, under suitable conditions, has an error incorporation rate equal to or lower than those associated with commonly used thermostable PCR polymerases such as Vent DNA polymerase or T7 DNA polymerase (from about $1.5 \times 10^{-5}$ to about $5.7 \times 10^{-5}$). In some embodiments, a Phi29 DNA polymerase or Phi29-like polymerase may be used for amplifying a DNA template. In some embodiments, a combination of a Phi29 DNA polymerase and a Taq DNA polymerase may be used for the circular DNA amplification.

Additional enzymes may be included in the isothermal amplification reaction mixture to minimize mis-incorporation events. For example, protein-mediated error correction enzymes, such as, MutS, may be added to improve the DNA polymerase fidelity either during or following the DNA polymerase reaction.

In some embodiments, one or more amplicons are produced from a circular target DNA template by rolling circle amplification (RCA). The amplification reagents including a DNA polymerase, primer, dNTPs and molecular crowding reagents and a buffer to maintain low salt concentration may be added to the target DNA to produce an amplification reaction mixture for initiating an RCA reaction. The amplification reaction mixture may further include reagents such as single-stranded DNA binding proteins and/or suitable amplification reaction buffers. After or during the amplification reaction, amplicons may be detected by any of the currently known methods for DNA detection. RCA may be a linear RCA (LRCA), exhibiting linear amplification kinetics (e.g., RCA using a single specific primer), or may be an exponential RCA (ERCA) exhibiting exponential amplification kinetics. RCA may also be performed using multiple primers (multiply primed rolling circle amplification or MPRCA) leading to hyper-branched concatemers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This often generates a discrete set of concatemeric, double-stranded nucleic acid amplification products. In some example embodiments, an RCA is performed in vitro under isothermal conditions using a suitable nucleic acid polymerase such as Phi29 DNA polymerase.

In some other embodiments, a linear DNA template may be amplified using MDA. Conventional methods of MDA using random primers and 75 mM salt at 30° C. can result in sequence-biased amplification and the formation of chimeric products. When the salt concentration is lowered in these reactions to 15 mM salt in an attempt to reduce production of chimeric sequences, the reaction kinetics slowed considerably. In contrast, usage of molecular crowding reagents and low salt condition in MDA reaction promoted faster DNA amplification kinetics and improved DNA sequence coverage and balance. Further, the decrease in $T_m$ of the target DNA:primer hybrid allows the MDA reaction to be performed under more stringent conditions, such as at a lower concentration of salt (e.g., 15 mM KCl as opposed to 75 mM under otherwise standard conditions) or allows use of more stringent buffers for high stringent hybridization conditions. Such stringent reaction further decreases unwanted reaction intermediates and products such as formation of chimeric products by self-hybridization.

Further, usage of molecular crowding reagent and low salt concentration in amplification reactions allows for robust amplification of trace DNA samples under a wider variety of conditions, including but not limited to, circulating plasma DNA, DNA isolated from formalin fixed paraffin-embedded (FFPE) samples, forensics DNA samples that have been exposed to environmental conditions or ancient DNA samples. The amplified library comprising the amplicons may further be used for targeted detection of amplified sequences via qPCR or sequencing.

In some embodiments, a kit for isothermal DNA amplification is provided. The kit comprises a DNA polymerase having strand displacement activity and a primer, a molecular crowding reagent, a buffer solution, wherein the buffer solution maintains a salt concentration of 10 to 30 mM.

In some embodiments, the kit comprises a Phi29 DNA polymerase. The kit may further comprise one or more random primers which have lower melting temperature.

The methods and kits described herein may be used for amplifying and analyzing DNA samples such as those for forensic analysis, bio-threat identification, or medical analysis. The sensitivity of the method allows for the whole-genome amplification of single bacterial and eukaryotic cells for whole genome amplification for downstream testing and analysis. Further, the use of molecular crowding reagents and low salt condition promote faster DNA amplification kinetics, higher sensitivity for low input DNA quantities, and results in less biased, more balanced amplification.

The following examples are disclosed herein for illustration only and should not be construed as limiting the scope of the invention. Some abbreviations used in the examples section are expanded as follows: "mg": milligrams; "ng": nanograms; "pg": picograms; "fg": femtograms; "mL": milliliters; "mg/mL": milligrams per milliliter; "mM": millimolar; "mmol": millimoles; "pM": picomolar; "pmol": picomoles; "µL": microliters; "min.": minutes and "h.": hours.

EXAMPLES

Example 1: Reaction Kinetics and Sensitivity of MDA Reactions of DNA from Single Cells in Presence of PEG and Low Salt Condition Cultures of *E. coli* MG1655 were grown to log phase in LB media, harvested by centrifugation, and washed three times using TEN buffer (10 mM Tris, pH 7.5, 100 mM NaCl, and 0.1 mM EDTA). After washing, cells were resuspended in buffer TEN+30% glycerol and serial dilutions were made. Cells were then stained with 10 µM FM1-43FX dye (F-35355, from Invitrogen, Life Technologies) for 10 minutes at room temperature, added stained cells into each of the wells of a transparent-bottom 384-well plate, and counted using an inverted fluorescent microscope (Nikon Eclipse TE2000-U). Following identification of wells containing single cells, lysis was initiated by addition of 2 µl of 0.2 M KOH, 50 mM DTT, 0.015% Tween-20 and freezing at −80° C. overnight. The following morning, plates were thawed and lysate was further incubated at 65° C. for 10 minutes, cooled, and neutralized by addition of 1 µl of 0.4M HCl, 0.6 M Tris, pH 7.5.

Amplification (GenomiPhi™) reactions were performed using a random hexamer primer in presence and absence of PEG 8000 and low salt condition to determine the effect of molecular crowding reagent and low salt condition on MDA reactions. GenomiPhi™ amplification reaction mixtures containing 50 mM HEPES, pH 8.0, 20 mM MgCl$_2$, 0.01% Tween-20, 1 mM TCEP, 40 µM random hexamer, SYBR Green I (Invitrogen) at 1:20,000 dilution, 20 µg/ml Phi29 polymerase, and the indicated concentrations of PEG-8000 and KCl (Table 1) were prepared by incubating at 30° C. for 1 hour to remove any small quantity of contaminating DNA.

Amplification reactions were initiated by addition of 400 µM dNTPs to the cell lysates. Reactions were incubated at 30° C. for 8 hours in a plate reader (Tecan), while taking fluorescence measurements at 5 min intervals to measure amplification kinetics. The amplification reaction was monitored real time by measuring the fluorescence increase over time in a Tecan plate reader (Tecan SNiPer, Amersham-Pharmacia Biotech). Reactions were then inactivated by heating at 65° C. for 20 minutes and amplified DNA was purified by ethanol precipitation. The average DNA yields as determined by quantitation by Pico Green (Invitrogen) are shown in table 1, wherein dN6 represents a hexamer primer having an oligonucleotide sequence of NNNN*N*N. The salt concentrations in these reactions are listed assuming that 20 mM of salt originates from the cell lysis and neutralization procedure. The remaining salt comes from additional KCl added to the reaction mixture. The average yield is from three 20 µl reactions, except for the clean GenomiPhi™ formulation in which only two reactions produced amplified product.

TABLE 1

The average DNA yields as determined by Pico Green Assay

| Formulation | Hexamer | 2.5% PEG-8000 | Salt (mM) | Avg. yield (µg) |
|---|---|---|---|---|
| Clean GPhi | dN6 | N | 75 | 1.8 |
| dN6 – PEG | dN6 | N | 20 | 3.28 |
| dN6 + PEG | dN6 | Y | 20 | 3.03 |

Figure 1B:
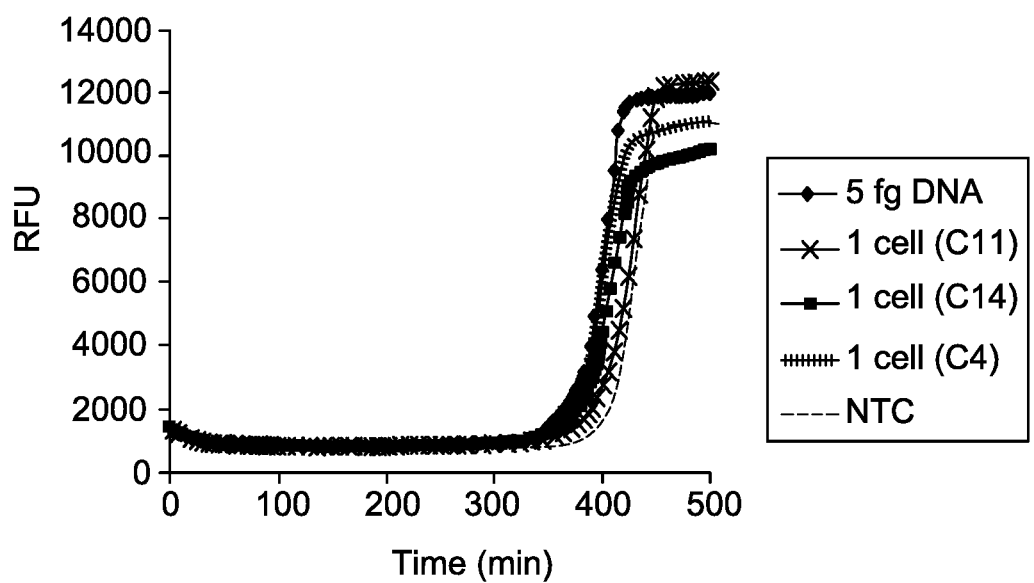
FIG. 1B illustrates the kinetics of an MDA reaction without molecular crowding reagents, in presence of low salt.
Figure 1C:
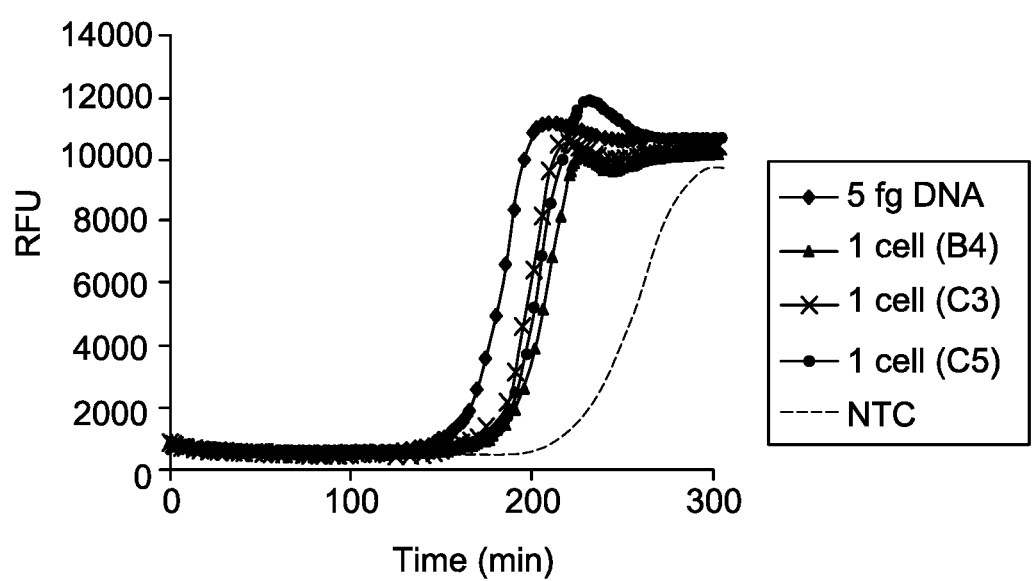
FIG. 1C illustrates the effectiveness of a molecular crowding reagent and low salt condition to increase the kinetics and sensitivity of an MDA reaction from a single cell.

Fluorescence measurements were taken at 5 min intervals of amplification reactions from 5 fg of purified *E. coli* DNA (approximately the amount of DNA from a single cell), from reactions containing lysed single cell, and from reactions in which no DNA was added (NTC) as shown in FIGS. 1A to 1C, wherein RFU, relative fluorescence units; was measured with respect to time. NTC represents the "no template control" wherein the amplification reaction was performed without the addition of a target DNA template. The reduction of salt in the dN6–PEG formulation allowed for all three single cells to be amplified and provided a higher average yield of amplified DNA product. FIGS. 1A, 1B and 1C illustrate the amplification kinetics of target nucleic acids using standard random hexamer primer in absence of PEG under high salt condition, in absence of PEG under low salt condition, and in presence of PEG under low salt condition, respectively. The amplification rate for no template control (NTC), 5 fg DNA, and each of the single cell samples were estimated by monitoring the time taken for the generation of detectable levels of amplicon products in each of the samples.

FIG. 1C shows an increased reaction kinetics and sensitivity of MDA reaction in presence of PEG under low salt condition. The amplification reaction in presence of PEG under low salt condition provided increased amplification speed (approximately 2.5-fold) and allowed femtogram (fg) quantities of DNA, and DNA from a single cell to be amplified efficiently. An analysis of the reaction kinetics (FIGS. 1A to 1C) showed that the amplification rates for the clean GenomiPhi™ formulation and the dN6–PEG formulation were approximately the same. However, upon addition of 2.5% PEG-8000 as in the dN6+PEG formulation, the amplification kinetics was dramatically improved, displaying an approximately 2.5-fold increase. In addition, there was a clear separation in amplification time between the single cells as compared with the no-template control, suggesting a higher quality of amplified product.

The kinetics and yield, unexpectedly, suggest that in spite of providing reaction conditions of low salt and presence of molecular crowding reagents, the amplification reaction containing PEG and low salt proceeded quickly and efficiently. Unlike the currently known methods, which disclose the condition of low salt prevents efficient primer hybridization, the present method showed in presence of both low salt and molecular crowding reagents, the reaction rate increases compared to the same at low salt condition without molecular crowding reagents. The reaction conditions which generally prevents efficient hybridization of primer-template, include but are not limited to, a low salt concentration, a high temperature and use of primers having a $T_m$ which is 8-10° C. lower than that of the reaction temperature. Additionally, analysis of the amplified product indicates that all regions of the template genomic DNA were amplified representatively, with no under-amplification of A/T rich regions, and over-amplification of G/C rich regions, which would be typically expected under conditions where the primer binding conditions were stringent, and only allowed for G/C rich primers to hybridize. Moreover, the presence of PEG as a molecular crowding agent and low salt condition did not inhibit binding of the primer and template DNA and extension by DNA polymerase, and strand displacement of the primer by the DNA polymerase during isothermal amplification. If PEG or low salt condition inhibited the hybridization of the primer-template, followed by initiation of extension by the DNA polymerase, the kinetics would have been slow, and yield would have been low.

Figure 2:
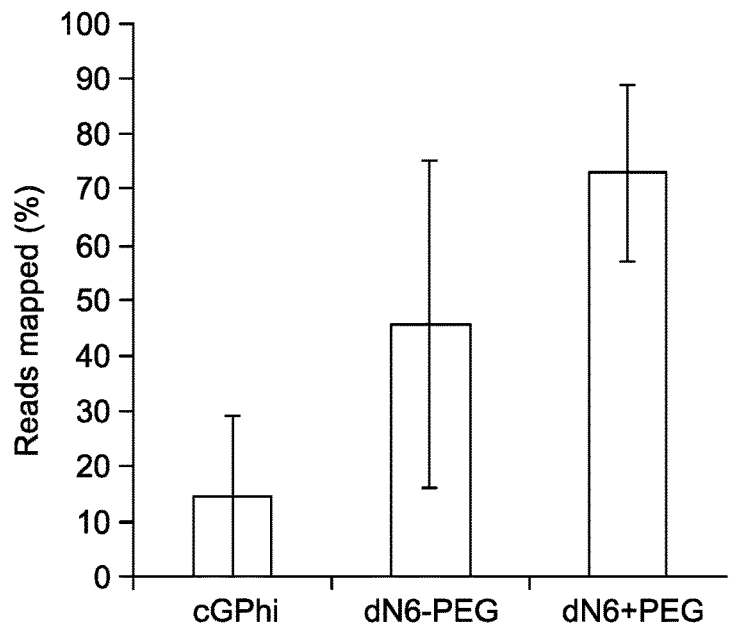
FIG. 2 illustrates the effectiveness of a molecular crowding reagent and low salt condition in reducing background non-specific amplification, allowing for a greater percentage of the total reads to be mapped to the target genome.

The amplified DNA from the single cell was processed into libraries and subjected to whole-genome sequencing using the Illumina HiSeq™ 2000 with paired-end reads and 100 base pair read lengths. Approximately 8 million to 16 million reads were obtained for each sample, which were then mapped to the *E. coli* MG1655 reference genome, as shown in FIG. 2. Raw reads were uploaded to DNANexus, which offers DNA analysis computing services and the reads were mapped to the *E. coli* MG1655 reference genome. Only reads that were mapped accurately were included in the analysis including reads that mapped repetitively. The standard deviation between the single cell replicates is indicated by the error bars, as shown in FIG. 2.

From FIG. 2, a clear difference for three different GenomiPhi™ amplification formulations in producing DNA reads that were mapped successfully. The lower salt concentration and the presence of PEG-8000 together allowed for the production of more target *E. coli* DNA and correspondingly less unmappable sequence.

Figure 3:
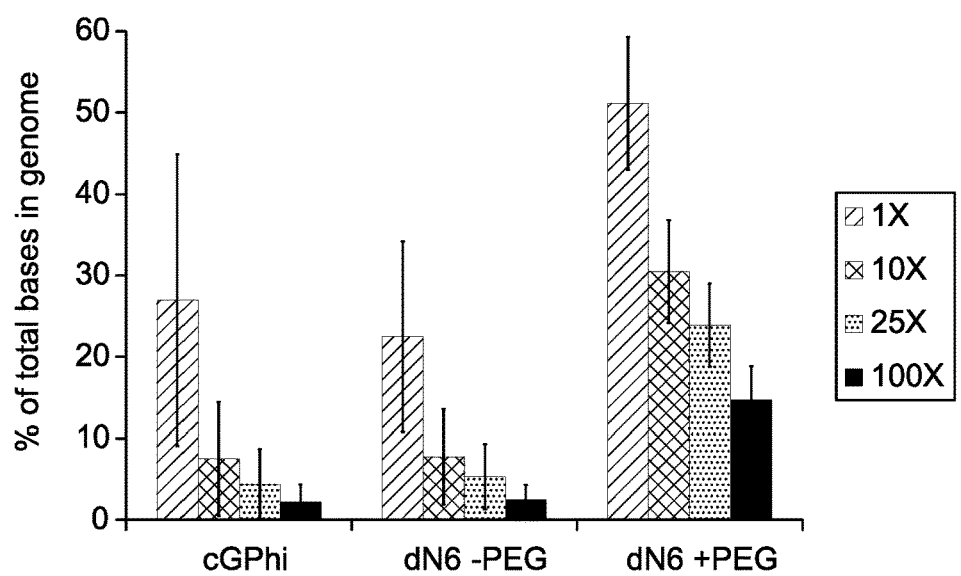
FIG. 3 illustrates the effectiveness of a molecular crowding reagent and low salt condition to increase the overall genome sequence coverage at varying depths and the amplification balance of DNA amplification reactions initiated from a single cell.

After mapping reads to the *E. coli* MG1655 reference genome, the percentage of bases in the total 4.6 Mb genome that were covered by at least the indicated number of reads (1×-100×) was calculated, as shown in FIG. 3, wherein the standard deviation between the single cell replicates is indicated by the error bars. In addition, the combination of low salt and the addition of PEG-8000 allowed for a greater degree of base coverage of the *E. coli* genome by the sequence read which was evident at a range of coverage depths from 1× to 100× (FIG. 3). This would allow for an improved ability to construct genome sequences of unknown sequence and for a more robust analysis in sequencing applications.

The above detailed description is exemplary and not intended to limit the invention of the application and uses of the invention. Throughout the specification, exemplification of specific terms should be considered as non-limiting examples. The singular forms "a", "an" and "the" include plural referents unless the context clearly dictates otherwise.

Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the invention. At the very least, and not as an attempt to limit the application of the doctrine of equivalents to the scope of the claims, each numerical parameter should at least be construed in light of the number of reported significant digits and by applying ordinary rounding techniques. Where necessary, ranges have been supplied, and those ranges are inclusive of all sub-ranges there between.

The invention may be embodied in other specific forms without departing from the spirit or essential characteristics thereof. The foregoing embodiments are selected embodiments or examples from a manifold of all possible embodiments or examples. The foregoing embodiments are therefore to be considered in all respects as illustrative rather than limiting on the invention. While only certain features of the invention have been illustrated and described herein, it is to be understood that one skilled in the art, given the benefit of this disclosure, will be able to identify, select, optimize or modify suitable conditions/parameters for using the methods in accordance with the principles of the invention, suitable for these and other types of applications. The precise use, choice of reagents, choice of variables such as concentration, volume, incubation time, incubation temperature, and the like may depend in large part on the particular application for which it is intended. It is, therefore, to be understood that the appended claims are intended to cover all modifications and changes that fall within the spirit of the invention. Further, all changes that come within the meaning and range of equivalency of the claims are intended to be embraced therein.

The invention claimed is:

1. A kit for amplifying a nucleic acid comprising:
   (a) a DNA polymerase having a strand displacement activity;
   (b) a molecular crowding reagent, wherein the molecular crowding reagent is a polyethylene glycol (PEG); and
   (c) a buffer solution that maintains a final salt concentration between 10 mM to 20 mM during amplification at a constant reaction temperature;
   further comprising a random primer;
   wherein the random primer is a random hexamer primer.

2. A kit for isothermal amplification of a nucleic acid comprising:
   (a) a DNA polymerase having a strand displacement activity;
   (b) a molecular crowding reagent; and
   (c) a buffer solution that maintains a salt concentration between 1 mM and 35 mM in an isothermal amplification reaction mixture,
   wherein the molecular crowding reagent is a polyethylene glycol (PEG);
   further comprising a random primer;
   wherein the random primer is a random hexamer primer.

3. The kit of claim 2, wherein the buffer provides a salt concentration between 10 mM and 30 mM in the isothermal amplification reaction mixture.

4. The kit of claim 2, wherein the buffer provides a salt concentration between 10 mM and 20 mM in the isothermal amplification reaction mixture.

5. The kit of claim 2, wherein the buffer provides a salt concentration of about 20 mM in the isothermal amplification reaction mixture.

6. The kit of claim 2, wherein the PEG is selected from a group consisting of PEG-400, PEG-2000, PEG-6000, PEG-8000, and combinations thereof.

7. The kit of claim 6, wherein the PEG is PEG-8000.

8. The kit of claim 7, wherein a concentration of the PEG-8000 in the isothermal amplification reaction mixture is about 2.5 wt %.

9. The kit of claim 8, wherein the buffer provides a salt concentration of 20 mM in the isothermal amplification reaction mixture.

10. The kit of claim 1, wherein the random hexamer primer has a general structure of (atN)(atN)(atN)(atN)(atN)*N, wherein (atN) represents any of 2-amino-deoxyadenosine (2-amino-dA), dC, dG, or 2-thio-deoxythymidine (2-thio-dT), and wherein *N represents a phosphorothioate-modified random nucleotide.

11. The kit of claim 1, wherein the random hexamer primer comprises at least one of a 2-amino-deoxyadenosine (2-amino-dA) or a 2-thio-deoxythymidine (2-thio-dT).

12. The kit of claim 2, wherein the DNA polymerase is a phi29 DNA polymerase.

13. The kit of claim 12 further comprising a random primer having a melting temperature of lower than 20° C. in the isothermal amplification reaction mixture.

14. The kit of claim 2 further comprising deoxyribonucleoside triphosphate (dNTP) mixture.

15. A kit for isothermal amplification of a nucleic acid comprising:
   (a) a phi29 DNA polymerase;
   (b) a molecular crowding reagent;
   (c) a buffer solution that maintains a salt concentration of about 20 mM in an isothermal amplification reaction mixture; and
   (d) a random hexamer primer having an oligonucleotide sequence NNNN*N*N, wherein the molecular crowding reagent is polyethylene glycol-8000 (PEG-8000), and wherein *N represents a phosphorothioate-modified random nucleotide.

16. The kit of claim 15, wherein a melting temperature of the random hexamer primer in the isothermal amplification reaction mixture is lower than 20° C.

17. The kit of claim 2, wherein the random hexamer primer has a general structure of (atN)(atN)(atN)(atN)(atN)*N, wherein (atN) represents any of 2-amino-deoxyadenosine (2-amino-dA), dC, dG, or 2-thio-deoxythymidine (2-thio-dT), and wherein *N represents a phosphorothioate-modified random nucleotide.

18. The kit of claim 2, wherein the random hexamer primer comprises at least one of a 2-amino-deoxyadenosine (2-amino-dA) or a 2-thio-deoxythymidine (2-thio-dT).

* * * * *